US00PP17001P2

(12) United States Plant Patent
Iwaki

(10) Patent No.: US PP17,001 P2
(45) Date of Patent: Aug. 15, 2006

(54) ***TORENIA* PLANT NAMED 'SUNRENICOPALAVE'**

(50) Latin Name: ***Torenia* sp.**
Varietal Denomination: Sunrenicopalave

(75) Inventor: Kazunari Iwaki, Shiga (JP)

(73) Assignee: Suntory Flowers Ltd., Tokyo (JP)

( * ) Notice: Subject to any disclaimer, the term of this patent is extended or adjusted under 35 U.S.C. 154(b) by 0 days.

(21) Appl. No.: 11/091,833

(22) Filed: Mar. 28, 2005

(51) Int. Cl.
*A01H 5/00* (2006.01)

(52) U.S. Cl. ..... Plt./263

(58) Field of Classification Search ..... Plt./263
See application file for complete search history.

*Primary Examiner*—Kent Bell
*Assistant Examiner*—Louanne Krawczewicz Myers
(74) *Attorney, Agent, or Firm*—C. A. Whealy

(57) ABSTRACT

A new and distinct cultivar of *Torenia* plant named 'Sunrenicopalave', characterized by its upright, outwardly spreading, semi-prostrate and uniformly mounded plant habit; freely branching and vigorous growth habit; large violet-colored flowers; freely and continuous flowering habit; and tolerance to high temperatures and rain.

1 Drawing Sheet

Botanical designation: *Torenia* sp.
Cultivar denomination: 'Sunrenicopalave'.

BACKGROUND OF THE INVENTION

The present Invention relates to a new and distinct cultivar of *Torenia* plant, botanically known as *Torenia* sp., and hereinafter referred to by the cultivar name Sunrenicopalave.

The new *Torenia* is a product of a planned breeding program conducted by the Inventor in Higashiomi, Shiga, Japan. The objective of the breeding program was to create new compact *Torenia* cultivars with attractive flower coloration.

The new *Torenia* originated from a cross-pollination made by the Inventor on Jun. 27, 2002 in Higashiomi, Shiga, Japan of the *Torenia* sp. cultivar Cyclone Burgundy, not patented, as the female, or seed, parent with the *Torenia* sp. cultivar *Torenia* Concolor, not patented, as the male, or pollen, parent. The new *Torenia* was discovered and selected by the Inventor as a flowering plant within the progeny of the stated cross-pollination in a controlled environment in Higashiomi, Shiga, Japan.

Asexual reproduction of the new cultivar by terminal cuttings at Higashiomi, Shiga, Japan since September, 2003, has shown that the unique features of this new *Torenia* are stable and reproduced true to type in successive generations.

SUMMARY OF THE INVENTION

Plants of the cultivar Sunrenicopalave have not been observed under all possible environmental conditions. The phenotype may vary somewhat with variations in environment such as temperature and light level without, however, any variance in genotype.

The following traits have been repeatedly observed and are determined to be the unique characteristics of 'Sunrenicopalave'. These characteristics in combination distinguish 'Sunrenicopalave' as a new and distinct cultivar of *Torenia:*

1. Upright, outwardly spreading, semi-prostrate and uniformly mounded plant habit.
2. Freely branching and vigorous growth habit.

3. Large violet-colored flowers.
4. Freely and continuous flowering habit.
5. Tolerant to high temperatures and rain.

Plants of the new *Torenia* can be compared to plants of the female parent, the cultivar Cyclone Burgundy. In side-by-side comparisons conducted in Higashiomi, Shiga, Japan, plants of the new *Torenia* differed from plants of the cultivar Cyclone Burgundy in the following characteristics:

1. Plants of the new *Torenia* were more mounded than and not as upright as plants of the cultivar Cyclone Burgundy.
2. Plants of the new *Torenia* were broader than plants of the cultivar Cyclone Burgundy.
3. Plants of the new *Torenia* and the cultivar Cyclone Burgundy differed in petal coloration as plants of the cultivar Cyclone Burgundy had red purple-colored petals.
4. Plants of the new *Torenia* flowered for a longer period of time than plants of the cultivar Cyclone Burgundy.

Plants of the new *Torenia* can be compared to plants of the male parent, the cultivar *Torenia* Concolor. In side-by-side comparisons conducted in Higashiomi, Shiga, Japan, plants of the new *Torenia* differed from plants of the cultivar *Torenia* Concolor in the following characteristics:

1. Plants of the new *Torenia* had larger leaves than plants of the cultivar *Torenia* Concolor.
2. Plants of the new *Torenia* had larger flowers than plants of the cultivar *Torenia* Concolor.
3. Plants of the new *Torenia* had lighter colored petals than plants of the cultivar *Torenia* Concolor.
4. Plants of the new *Torenia* had shorter peduncles than plants of the cultivar *Torenia* Concolor.

Plants of the new *Torenia* can also be compared to plants of the *Torenia* sp. cultivar Sunrenibu, disclosed in U.S. Plant Pat. No. 10,119. In side-by-side comparisons conducted in Higashiomi, Shiga, Japan, plants of the new *Torenia* differed from plants of the cultivar Sunrenibu in the following characteristics:

1. Plants of the new *Torenia* were more mounding than plants of the cultivar Sunrenibu.
2. Plants of the new *Torenia* were not as broad as plants of the cultivar Sunrenibu.
3. Plants of the new *Torenia* had larger leaves and flowers than plants of the cultivar Sunrenibu.
4. Plants of the new *Torenia* were more freely flowering than plants of the cultivar Sunrenibu.
5. Plants of the new *Torenia* had lighter colored petals than plants of the cultivar Sunrenibu.

BRIEF DESCRIPTION OF THE PHOTOGRAPHS

The accompanying colored photographs illustrate the overall appearance of the new cultivar, showing the colors as true as it is reasonably possible to obtain in colored reproductions of this type. Colors in the photographs may differ slightly from the color values cited in the detailed botanical description which accurately describe the actual colors of the new *Torenia*.

The photograph at the top of the sheet is a side perspective view of a typical plant of 'Sunrenicopalave'.

The photograph at the bottom of the sheet is a close-up view of typical flowers and leaves of 'Sunrenicopalave'.

DETAILED BOTANICAL DESCRIPTION

The aforementioned photographs, following observations and measurements describe plants grown in Higashiomi, Shiga, Japan in an outdoor nursery and under commercial production practices during the summer. Plants were grown in 15-cm containers and were about four months old when the photographs and description were taken. During the production of the plants, day temperatures averaged 23° C. and night temperatures averaged 15° C. Plants were pinched one time in the spring. In the following description, color references are made to The Royal Horticultural Society Colour Chart, 2001 Edition, except where general terms of ordinary dictionary significance are used.

Botanical classification: *Torenia* sp. cultivar Sunrenicopalave.

Parentage:

*Female, or seed, parent.*—*Torenia* sp. cultivar Cyclone Burgundy, not patented.

*Male, or pollen, parent.*—*Torenia* sp. cultivar *Torenia* Concolor, not patented.

Propagation:

*Type.*—By terminal cuttings.

*Time to initiate roots.*—About one week at 20 to 25° C.

*Time to produce a rooted plant.*—About three to four weeks at 20 to 25° C.

*Root description.*—Fine, fibrous, fleshy; pale brown in color.

*Rooting habit.*—Freely branching.

Plant description:

*Plant form/habit.*—Upright, outwardly spreading, semi-prostrate and mounded plant habit; broadly inverted triangle; vigorous growth habit. Freely branching habit; dense and bushy growth habit.

*Plant height.*—About 17.4 cm.

*Plant width* (*spread*).—About 58 cm.

*Lateral branches.*—Length: About 30.6 cm. Diameter: About 1.9 mm. Internode length: About 5.8 cm. Strength: Strong. Texture: Pubescent. Color: 144B.

*Foliage description.*—Arrangement: Opposite, simple; sessile. Length: About 2.5 cm. Width: About 2.1 cm. Shape: Ovate. Apex: Obtuse. Base: Cordate. Margin: Crenate. Texture, upper and lower surfaces: Pubescent. Venation pattern: Pinnate; reticulate. Color: Developing and fully expanded leaves, upper surface: 137B; venation, similar to lamina. Developing and fully expanded leaves, lower surface: 147B; venation, similar to lamina.

Flower description:

*Flower type/habit.*—Single flowers with bilabiate corolla and tubular calyx: flowers face mostly outward. Freely flowering habit with numerous flowers per plant.

*Fragrance.*—None detected.

*Natural flowering season.*—Continuously flowering from May to September in Japan. Flowers not persistent.

*Postproduction longevity.*—Flowers last about four days on the plant.

*Flower buds.*—Height: About 1.6 cm. Diameter: About 6 mm. Shape: Lenticular. Color: 144A.

*Flowers.*—Diameter: About 3.4 cm by 2.8 cm. Depth: About 2.2 cm.

*Petals.*—Quantity per flower: Typically four in a single whorl; petals fused at the base. Lobe length, upper and lower petals: About 1.1 cm. Lobe length, lateral petals: About 9 mm. Lobe width, upper petal: About 2.1 cm. Lobe width, lateral petals: About 1.3 cm. Lobe width, lower petal: About 1.4 cm. Shape: Elliptic. Apex: Rotund. Margin: Entire; undulate. Texture, upper and lower surfaces: Smooth, glabrous; satiny. Color: Developing and fully expanded petals, upper surface: N87A; color becoming closer to N87B with development. Developing and fully expanded petals, lower surface: N87B. Throat: 91B; longitudinal lines, N79B. Tube: N87B.

*Sepals.*—Quantity per flower: Four, fused; tubular calyx. Calyx length: About 1.5 mm. Calyx diameter: About 5.6 mm. Shape: Narrowly oblong. Apex: Acute. Margin: Entire. Texture, upper and lower surfaces: Smooth, glabrous. Color, immature, upper and lower surfaces: 144A. Color, mature, upper and lower surfaces: 144A.

*Peduncles.*—Length: About 2.8 mm. Diameter: About 1.1 mm. Texture: Pubescent. Color: 144A.

*Reproductive organs.*—Stamens: Quantity per flower: Typically four. Anther shape: Ellipsoidal. Anther length: Less than 1 mm. Anther color: 76B. Pollen amount: Moderate. Pollen color: N155A. Pistils: Quantity per flower: Typically one. Stigma shape: Elliptic. Stigma color: 69C. Style length: About 1.8 cm. Style color: 69C. Ovary color: 144A.

*Seed/fruit.*—Seed and fruit development have not been observed.

Disease/pest resistance: Compared to other known cultivars and selections of *Torenia*, plants of the new *Torenia* have been noted to be moderately resistant to Powdery Mildew and significantly resistant to Red Spider Mites. Plants of the new *Torenia* have not been observed to be resistant to other pathogens and pests common to *Torenia*.

Garden performance: Plants of the new *Torenia* have been observed to have good garden performance and tolerate rain, wind and temperatures from 5 to 30° C.

It is claimed:

1. A new and distinct cultivar of *Torenia* plant named 'Sunrenicopalave', as illustrated and described.

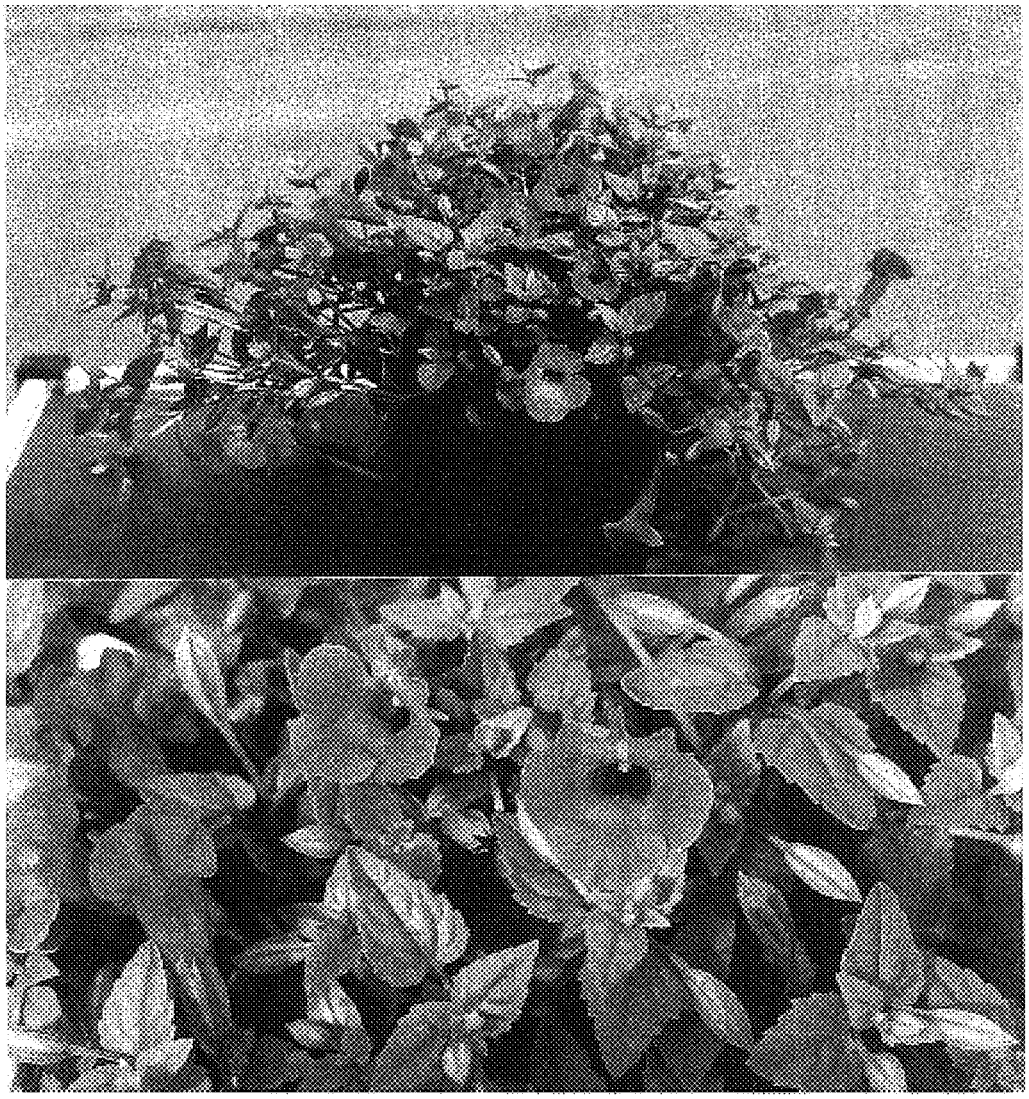

* * * * *